US007052867B2

(12) United States Patent
Kwon et al.

(10) Patent No.: US 7,052,867 B2
(45) **Date of Patent: *May 30, 2006**

(54) EXPRESSION AND SECRETION VECTOR FOR HUMAN INTERFERON ALPHA AND PROCESS FOR PRODUCING HUMAN INTERFERON ALPHA BY EMPLOYING SAME

(75) Inventors: Se-Chang Kwon, Seoul (KR); Sung-Youb Jung, Seoul (KR); Ki-Doo Choi, Seoul (KR); Cha-Soon Kim, Yongin-shi (KR); Sung-Min Bae, Seoul (KR); Gwan-Sun Lee, Seoul (KR)

(73) Assignee: Hanmi Pharm. Co., Ltd. (KR)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 428 days.

This patent is subject to a terminal disclaimer.

(21) Appl. No.: 10/182,040

(22) PCT Filed: Jan. 19, 2001

(86) PCT No.: PCT/KR01/00097

§ 371 (c)(1),
(2), (4) Date: Jul. 18, 2002

(87) PCT Pub. No.: WO01/57217

PCT Pub. Date: Aug. 9, 2001

(65) Prior Publication Data

US 2004/0151695 A1 Aug. 5, 2004

(30) Foreign Application Priority Data

Jan. 19, 2000 (KR) ................................ 2000-2434

(51) Int. Cl.
*C12P 21/06* (2006.01)
*C12N 15/00* (2006.01)
*C12N 15/21* (2006.01)

(52) U.S. Cl. ................ 435/69.1; 435/320.1; 435/69.51

(58) Field of Classification Search ............... 435/69.1, 435/320.1

See application file for complete search history.

(56) References Cited

U.S. PATENT DOCUMENTS 5,470,719 A 11/1995 Meng et al.
6,605,697 B1 * 8/2003 Kwon et al. ................ 530/300

FOREIGN PATENT DOCUMENTS

| | | | |
|---|---|---|---|
| EP | 0 626 448 A2 | | 5/1994 |
| JP | 61092575 | | 5/1986 |
| JP | 63230089 | | 9/1988 |
| JP | 7135992 | | 5/1995 |
| WO | WO 00/15661 | * | 3/2000 |

OTHER PUBLICATIONS

Riley et al., Pharmacogenomics (2000), vol. 1(1), pp. 39-47 (esp. p. 40 paragraph 1).*

Joseph Gennity, et al., Signal Peptide Mutants of *Escherichia coli,* Journal of Bioenergetics and Biomembranes, 22(3): 233-269, 1990.

Joel Goldstein, et al., Enhancement of Protein Translocation across the Membrance by Specific Mutations in the Hydrophobic Region of the Signal Peptide, Journal of Bacteriology, Mar. 1990, pp. 1225-1231, vol. 172, No. 3.

Tilman Voss, et al., Periplasmic expression of human interferon-a2c in *Escherichia coli* results in a correctly folded molecule, Biochem. J., (1994) 298, pp. 719-725.

Barbara K. Klein, et al., Effects of signal peptide changes on the secretion of bovine somatotropin (bST) from *Escherichia coli,* Protein Engineering, vol. 5, No. 6, pp. 511-517, 1992.

Hisashi Yasueda, et al., High-Level Direct Expression of Semi-Synthetic Human Interleukin-6 in *Escherichia coli* and Production of N-Terminus Met-Free Product, Biotechnology, vol. 8, Nov. 1990, pp. 1036-1040.

* cited by examiner

*Primary Examiner*—Janet L. Andres
*Assistant Examiner*—Jegatheesan Seharaseyon
(74) *Attorney, Agent, or Firm*—Anderson Kill & Olick, PC

(57) ABSTRACT

Disclosed in this invention are an expression vector for the secretive production of human interferon alpha (hIFNα) comprising a polynucleotide encoding a modified *E. coli* thermostable enterotoxin II signal sequence and a polynucleotide encoding hIFNα ligated to the 3'-end thereof; a microorganism transformed with the expression vector; and a process for secretively producing human interferon by culturing the microorganism, the process being capable of secreting a soluble form of active hIFNα, which does not contain an additional methionine residue at its N-terminal, into the periplasm of an *E. coli* cell.

11 Claims, 5 Drawing Sheets

EXPRESSION AND SECRETION VECTOR FOR HUMAN INTERFERON ALPHA AND PROCESS FOR PRODUCING HUMAN INTERFERON ALPHA BY EMPLOYING SAME

FIELD OF THE INVENTION

The present invention relates to an expression vector for the secretive production of human interferon alpha (hIFNα) comprising a polynucleotide encoding a modified *E. coli* thermostable enterotoxin II signal sequence and a polynucleotide encoding hIFNα ligated to the 3'-end thereof; a microorganism transformed with the expression vector; and a process for secretively producing hIFNα having no methionine residue added at its N-terminal in the periplasm of *E. coli* cell.

BACKGROUND OF THE INVENTION

Isaacs and Lindenmann reported in 1957 that when chicken is infected with influenza virus A, a viral replication inhibitory factor designated interferon is produced (Isaacs, K and Lindenmann, *J. Proc. R. Soc. Lond*., B147:258–267, 1957).

Human interferons are cytokine proteins which inhibit in vivo immune response or viral replication and they are classified as interferon alpha (IFNα), interferon beta (IFNβ) and interferon gamma (IFNγ) according to cell types producing them (Kirchner, H. et al., *Tex. Rep. Biol. Med.,* 41:89–93, 1981; Stanton, G. J. et al., *Tex. Rep. Biol. Med.,* 41:84–88, 1981).

It is well-known that these interferons work together to exert synergic effects in the manifestation of anti-viral, anti-cancer, NK (natural killer) cell activation and marrow cell inhibition activities (Klimpel, et al. *J. Immunol.,* 129: 76–78, 1982; Fleischmann, W. R. et al., *J. Natl. Cancer Inst.,* 65:863–966, 1980; Weigent, et al., *Infec. Immun.,* 40:35–38, 1980). In addition, interferons act as regulatory factors of the expression, structure and function of genes in the cell, and show a direct anti-proliferating effect.

IFNα is produced when leukocyte is stimulated by B cell mitogen, virus or cancer cells. Up to now, there have been reported genes that encode more than 20 species of interferons, each comprising 165 or 166 amino acids.

IFNα used for early clinical tests were obtained from buffy coat leukocyte stimulated by Sendai virus and its purity was only less than 1% (Cantell, K. and Hirvonen, *Tex. Rep. Biol. Med.,* 35:138–144, 1977).

It has become possible to produce a large quantity of IFNα having biophysical activity by gene recombinant techniques in the 1980' (Goedell, D. V. et al., *Nature,* 287:411–416, 1980). Clinical tests using the recombinant hIFNα have shown that it is effective in treating various solid cancers, particularly bladder cancer, kidney cancer, HIV related Kaposi's sarcoma, etc. (Torti, F. M., *J. Clin. Oncol.,* 6:476–483, 1988; Vugrin, D., et al., *Cancer Treat. Rep.,* 69:817–820, 1985; Rios, A., et al., *J. Clin. Oncol.,* 3:506–512, 1985). It is also effective for the treatment of hepatitis C virus (Davis, G. G., et al., *N. Engl. J. Med.,* 321:1501–1506, 1989), and its applicable range as a therapeutic agent is expanding day by day.

The result of cloning IFNα gene from leukocyte has shown that IFNα is encoded by a group of at least 10 different genes. This indicates that the DNA sequences of the genes do not produce one kind of protein but that IFNα is a mixture of subtype proteins having similar structures. Such subtype proteins are named IFNα-1, 2, 3, and so on (*Nature,* 290:20–26, 1981).

Among the several types of interferons, hIFNα purified from human leukocyte has a molecular weight of 17,500 to 21,000, and a very high native activity of about $2\times10^8$ IU/mg protein. In vivo IFNα is a protein consisting of 165 amino acids. It is designated IFNα-2a (SEQ ID NO: 1) in case the $23^{rd}$ amino acid is lycine, and IFNα-2b (SEQ ID NO : 2) in case the $23^{rd}$ amino acid is arginine. In the beginning hIFNα was produced by a process using a cell culture method. However, this process is unsuitable for commercialization because of its low productivity of about 250 ug/L.

To solve this problem, processes for recovering a large quantity of interferon from microorganisms by using gene recombinant techniques have been developed and used to date.

The most widely employed is a process using *E. coli* which produces IFNα consisting of 166 or 167 amino acids according to the characteristics of the *E. coli* cell. These products have an extra methionine residue added at the N-terminal by the action of the ATG codon existing at the site of initiation codon. However, it has been reported that the additional methionine residue can trigger harmful immune response, in the case of human growth hormone (EP Patent Publication No. 256,843).

In addition, most of the expressed IFNα accumulates in cytoplasm in the form of insoluble inclusion bodies and must be converted into an active form through refolding during a purification process. As such a refolding process is not efficient, IFNα exists partially in a reduced form, or forms an intermolecular disulfide coupling body or a defective disulfide coupling body. It is difficult to remove these by-products, which cause a markedly low yield. In particular, it is extremely difficult to remove undesirable interferon by-products such as misfolded interferons.

Recently, in order to solve the above mentioned problems associated with the production of a foreign protein within a microbial cell, various efforts have been made to develop a method based on efficient secretion of a soluble form of the target protein carrying no extra methionine added to the N-terminal.

In this method, a desired protein is expressed in the form of a fusion protein which carries a signal peptide attached to its N-terminal. When the fusion protein passes through the cell membrane, the signal peptide is removed by an enzyme in *E. coli* and the desired protein is secreted in a native form.

The secretive production method is more advantageous than the microbial production method in that the amino acid sequence and the higher structure of the produced protein are usually identical to those of the wild-type. However, the yield of a secretive production method is often quite low due to its unsatisfactory efficiencies in both the membrane transport and the subsequent purification process. This is in line with the well-known fact that the yield of a mammalian protein produced in a secretory mode in prokaryotes is much lower than that of a prokaryotic protein produced in the same mode in prokaryotes. Therefore, it has been attempted to develop a more efficient secretory production method. For instance, Korean Patent Publication No. 93-1387 discloses an attempt to mass-produce IFNα using the signal peptide of *E. coli* alkaline phosphatase, but the yield was very low at $10^9$ IU/L culture medium (10 ug/L culture medium). Therefore, there has been a keen interest in developing a method which is capable of producing soluble IFNα having no additional methionine residue added at the N-terminal, using a microorganism on a large scale.

The present inventors have previously generated a new signal peptide of *E. coli* thermostable enterotoxin II (Korean Patent Application No. 98-38061 and 99-27418) and found that this new secretory signal peptide can be used for the mass-production of the native form of IFNα. Namely, the present inventors have constructed an expression vector containing a gene obtained by ligating IFNα encoding gene instead of enterotoxin II encoding gene to the modified *E. coli* secretory signal peptide, and developed a secretory production method of IFNα having a native biological activity via the microbial secretory system by culturing the microorganism transformed with said expression vector.

SUMMARY OF THE INVENTION

Accordingly, it is an object of the present invention to provide an expression vector which can secretively produce human interferon alpha (hIFNα).

It is another object of the present invention to provide a microorganism transformed with said expression vector.

It is a further object of the present invention to provide a process for producing a soluble form of hIFNα using said microorganism, which has no extra methionine residue attached to the amino terminus.

BRIEF DESCRIPTION OF THE DRAWINGS

The above and other objects and features of the present invention will become apparent from the following description of the invention taken in conjunction with the following accompanying drawings; which respectively show:

FIG. 1: the procedure for constructing vector pT-IFNα-2a;

FIG. 2: the procedure for constructing vector pT14SIα-2a;

FIG. 3: the procedure for constructing vector pT14SSIα-2a;

DETAILED DESCRIPTION OF THE INVENTION

Figure 1:
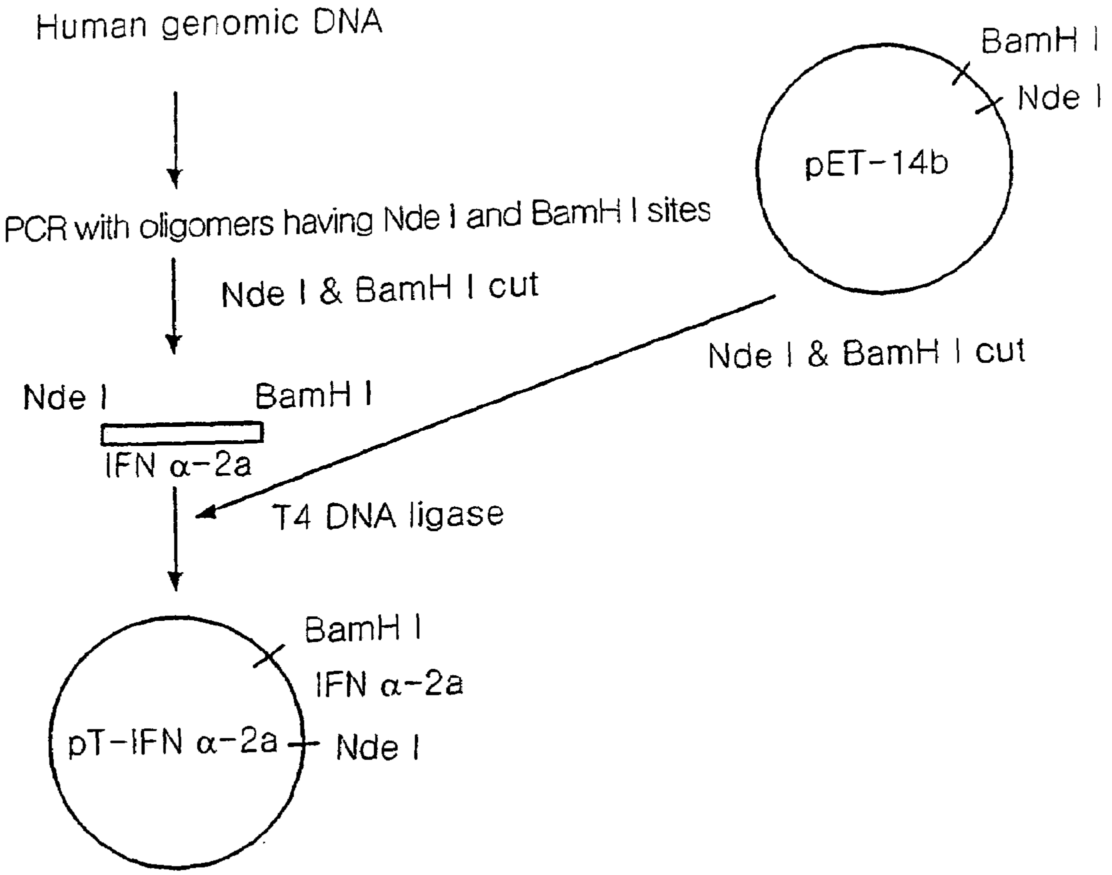

According to one aspect of the present invention, there is provided an expression vector for the secretive production of hIFNα comprising a polynucleotide encoding a modified thermostable enterotoxin II signal sequence (hereinafter, as referred as to 'STII mutant') and a polynucleotide encoding hIFNα ligated to the 3'-end thereof.

The polynucleotide encoding hIFNα used for constructing the expression vector of the present invention may be any one of polynucleotides encoding random hIFNα subtypes such as native hIFNα-2a (SEQ ID NO: 1), IFNα-2b (SEQ ID NO : 2), IFNα-1 and IFNα-3, and it may also be a recombinant polynucleotide which has a modified base sequence that encodes any of the above IFNα subtypes.

The polynucleotide encoding the modified *E. coli* thermostable enterotoxin II signal sequence of the present invention, which is ligated to the front of the 5'-end of the polynucleotide encoding hIFNα and used for the purpose of the secretive production of hIFNα, may be a polynucleotide encoding a mutant derivable by replacing one or more of the amino acids of *E. coli* thermostable enterotoxin II signal sequence described in SEQ ID NO: 3, preferably one or more of the $4^{th}$, $20^{th}$ and $22^{nd}$ amino acids thereof with other amino acid(s). Examples of such polynucleotides encode mutants obtained by replacing: the $4^{th}$ amino acid with threonine ([$Thr^4$]STII); the $4^{th}$ amino acid with threonine and the $22^{nd}$ amino acid with glutamine, respectively ([$Thr^4$, $Gln^{22}$]STII); the $4^{th}$ amino acid with threonine, the $20^{th}$ amino acid with valine and the $22^{nd}$ amino acid with glutamine, respectively ([$Thr^4$, $Val^{20}$, $Gln^{22}$]STII); and the $4^{th}$ amino acid with threonine and the $20^{th}$ amino acid with valine, respectively ([$Thr^4$, $Val^{20}$]SDII) in the *E. coli* thermostable enterotoxin II signal sequence (STII) described in the SEQ ID NO: 3, and preferred polynucleotide sequences are SEQ ID NOS: 4, 5, 6 and 7. However, it is known that several different polynucleotides encoding the mutants of the present invention may exist due to the codon degeneracy, and, specifically, a polynucleotide modified by introducing preferred codons of *E. coli* without any change of amino acid sequence can be used for promoting the expression rate of IFNα.

In addition, the expression vector of the present invention may further comprise *E. coli* thermostable enterotoxin II Shine-Dalgarno sequence (SD sequence, SEQ ID NO: 8) or its mutant ligated to the front of the 5'-end of the polynucleotide encoding the modified thermostable enterotoxin II signal sequence. As compared with an wild-type which has 7 bases (TGATTTT) following GAGG of the 5'-end in the *E. coli* thermostable enterotoxin II SD sequence described in the SEQ ID NO: 8, the mutant of SD sequence has a shorter sequence of 6 or 5 bases. The use of this mutant can increase the secretive expression rate of IFNα. However, when said base sequence becomes shorter than 4 bases, the expression rate decreases markedly. A specific example of a preferred mutant that can be used in the present invention is the *E. coli* thermostable enterotoxin II SD sequence mutant having the nucleotide sequence of SEQ ID NO: 9.

The promoter used in preparing the expression vector of the present invention may be any of those which can express a heterologous protein in a microorganism host. Specifically, lac, Tac, and arabinose promoter is preferred when the heterologous protein is expressed in *E. coli.*

This invention also provides transformed microorganisms which may be obtained e.g., by transforming such *E. coli* strains as *E. coli* BL21(DE3) (Novagen, USA) or *E. coli* XL-1 blue (Novagen, USA) with said expression vector. Examples of the present invention provide such transformed microorganisms: *E. coli* BL21(DE3)/pT140SSIα-2a-4T ("HM 10603"), *E. coli* BL21(DE3)/pT140SSIα-2a-4T22Q ("UM 10611"), *E. coli* BL21(DE3)/pT140SSIα-2b-4T ("HM 10703") and *E. coli* BL21(DE3)/pT140SSIα-2b-4T22Q ("HM 10711"). The above transformed microorganisms are deposited in Korean Culture Center of Microorganisms (KCCM) (Address; Yurim Bldg., 361-221, Hongje 1-dong, Seodaemun-gu, Seoul 120-091, Republic of Korea) on Dec. 23, 1999 under accession numbers KCCM-10175, KCCM-10176, KCCM-10177 and KCCM-10178, respectively, in accordance with the terms of the Budapest Treaty on the International Recognition of the Deposit of Microorganism for the Purpose of Patent Procedure.

In accordance with another aspect of this invention, there is also provided a process for secretively producing hIFNα having no additional methionine residue attached at the N-terminal, into the periplasm of *E. coli* by culturing the transformed microorganism under an appropriate culture condition which may be the same as the conventional culture condition used for transformed microorganisms.

hIFNα secretively produced by the process of the present invention comprises random hIFNα subtypes such as IFNα-1, IFNα-3 and so on, as well as native hIFNα-2a (SEQ ID NO: 1) and hIFNα-2b (SEQ ID NO: 2) consisting of 165 amino acids. In addition, the process of the present invention can be applied to the production of any other interferon such as hIFNβ and hIFNγ.

According to the process of the present invention, 80% or more of IFNα produced by the inventive *E. coli* transformant is secreted into the periplasm at a high productivity of more than 1 g/L. The produced IFNα has the same amino acid sequence as that of native IFNα which has no additional amino acid attached at the N-terminal, and shows a biological activity equal to that of native IFNα.

The following Examples are included to further illustrate the present invention without limiting its scope.

REFERENCE EXAMPLE

IFNα-2a Gene and Construction of a Vector Containing Same

A gene encoding hIFNα-2a was prepared by carrying out PCR using human genomic DNA as a template and SEQ ID NOS: 10 and 11 as primers. The primer of SEQ ID NO: 10 was designed to provide an NdeI restriction site (5'-CATATG-3') upstream from the codon for the first amino acid (cysteine) codon of native hIFNα, and the primer of SEQ ID NO: 11, to provide a BamHI restriction site (5'-GGATCC-3') downstream from the termination codon thereof.

The amplified PCR product was cleaved with NdeI and BamHI to obtain a DNA fragment encoding hIFNα-2a. The DNA fragment was inserted into the NdeI/BamHI site of vector pET-14b (Novagen, USA) to obtain vector pT-IFNα-2a.

FIG. 1 shows the above procedure for constructing vector pT-IFNα-2a.

COMPARATIVE EXAMPLE 1

Construction of a Vector Containing Enterotoxin Signal Sequence and IFNα-2a Genes To prepare *E. coli* enterotoxin II signal sequence gene, the pair of complementary oligonucleotides of SEQ ID NOS: 12 and 13 were designed based on the previously known nucleotide sequence of *E. coli* enterotoxin II signal peptide, and synthesized using a DNA synthesizer (Model 380B, Applied Biosystem, USA). The above oligonucleotides were designed to provide a BspHI restriction site (complementary sites to an NdeI restriction site) upstream from the initiation codon of *E. coli* enterotoxin II and a MluI restriction site introduced by a silent change at the other end. Both oligonucleotides were annealed at 95° C. to obtain a blunt-ended DNA fragment having a nucleotide sequence encoding *E. coli* enterotoxin II signal sequence. The above DNA fragment was inserted into the SmaI site of vector pUC19 (BioLabs, USA) to obtain vector pUC19ST.

In addition, vector pT-IFNα-2a containing IFNα-2a gene obtained in Reference Example was subjected to PCR using the primers of SEQ ID NOS: 14 and 15 to ligate the enterotoxin signal peptide to IFNα-2a gene. The primer of SEQ ID NO: 14 was designed to correspond to the 5'-end of IFNα-2a gene, and the primer of SEQ ID NO: 15, to provide a BamHI restriction site (5'-GGATCC-3') downstream from the termination codon thereof. The DNA fragment containing the polynucleotide, which encodes native IFNα-2a, was amplified by PCR using the above polynucleotide primers. The amplified DNA fragment was cleaved with MluI and BamHI to obtain an IFNα-2a DNA fragment having MluI/BamHI ends.

Meanwhile, vector pUC19ST containing the enterotoxin signal peptide was cleaved with MluI and then digested with BamHI to obtain a vector fragment having MluI/BamHI ends. The vector fragment was ligated to the IFNα-2a DNA fragment to construct vector pUC19SIFNα-2a.

Figure 2:
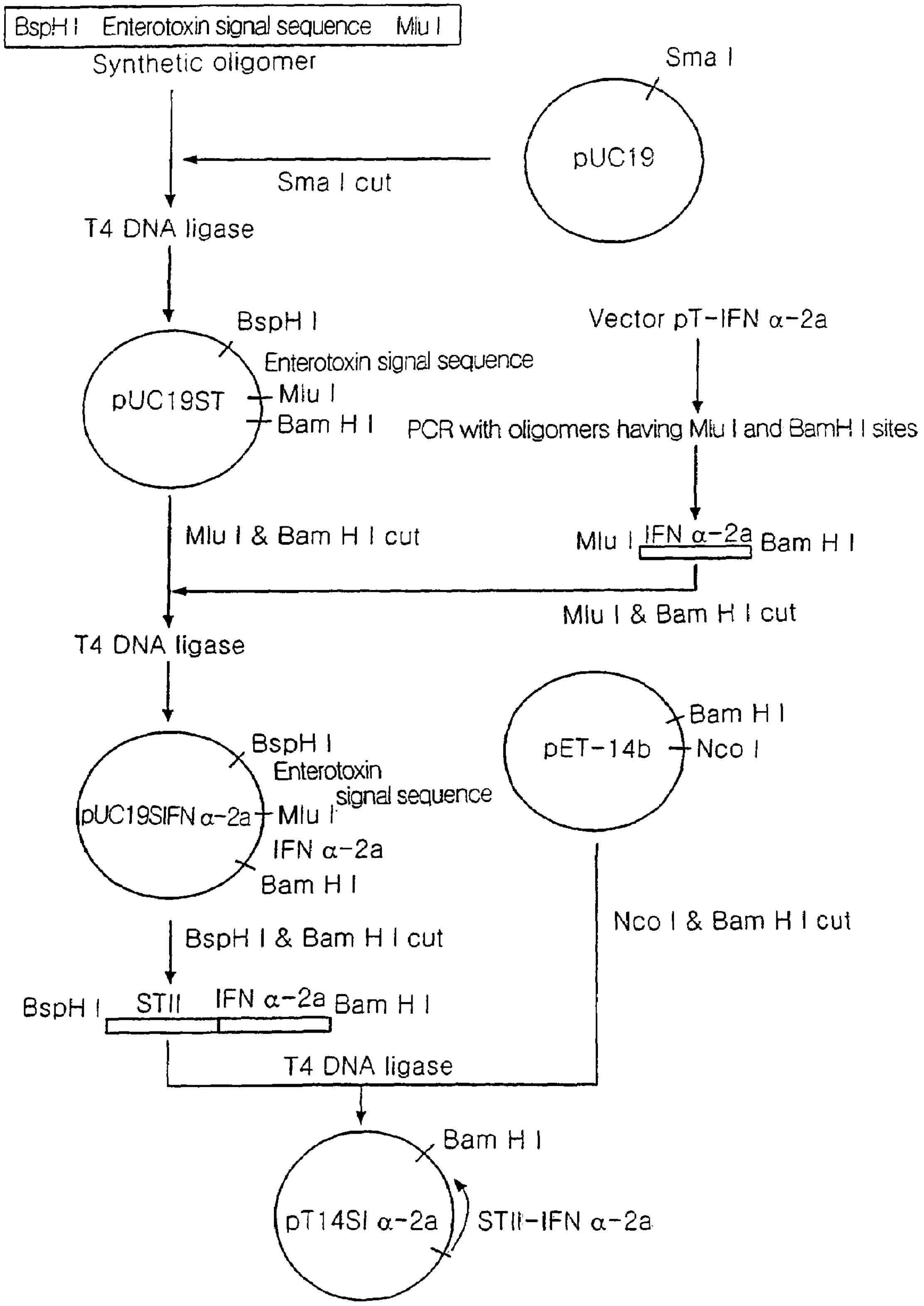

Vector pUC19SIFNα-2a was cleaved with BspHI and BamHI to obtain a DNA fragment (564 bp). The DNA fragment was inserted at the NcoI/BamHI section of vector pET-14b (Novagen, USA) to obtain vector pT14SIα-2a. FIG. 2 shows the above procedure for constructing vector pT14SIα-2a.

Subsequently, *E. coli* BL21(DE3) strain was treated with 70 mM calcium chloride solution to prepare competent *E. coli*, and then, vector pT141α-2a in 10 mM Tris buffer (pH 7.5) was added thereto. An *E. coli* transformant expressing IFNα-2a was selected by a conventional method which exploits the sensitivity of the transformed vector toward antibiotics, and designated *E. coli* HM 1 0600.

In addition, vector pT14SIα-2a was subjected to PCR using the primers of SEQ ID NOS: 16 and 17 to amplify a DNA fragment obtained by ligating the Shine-Dalgarno sequence of the enterotoxin, the enterotoxin signal peptide, and IFNα-2a gene, in that order, and then the DNA fragment was cleaved with XbaI and BamHI to obtain an insert.

Figure 3:
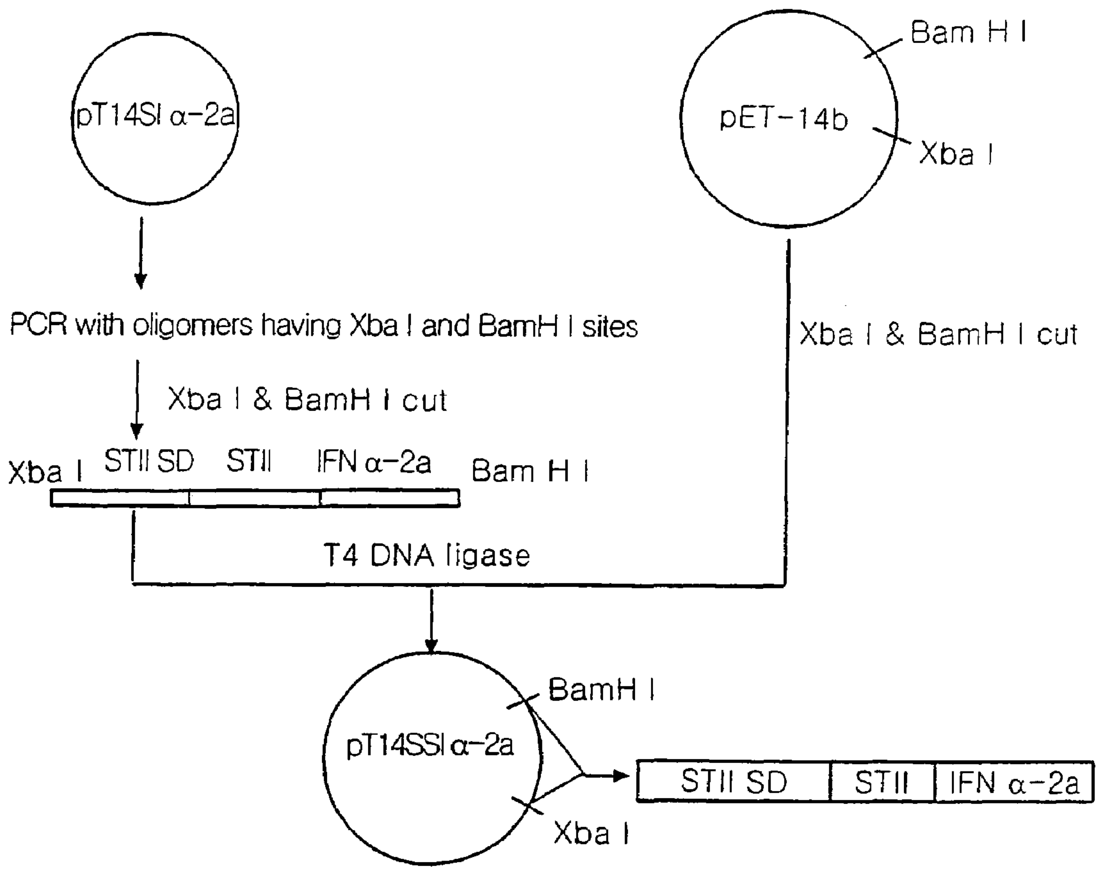

The insert was ligated into the XbaI/BamHI section of vector pET-14b (Novagen, USA) to construct vector pT14SSIα-2a. FIG. 3 displays the above procedure for constructing vector pT13SSIα-2a. *E. coli* BL21(DE3) (Stratagene, USA) was transformed with vector pT14SSIα-2a to obtain a transformant designated *E. coli* HM 10601.

COMPARATIVE EXAMPLE 2

Construction of a Vector Containing Enterotoxin Signal Sequence and IFNα-2b Genes The $23^{rd}$ lycine codon of IFNα-2a gene in vector pT14SSIα-2a was replaced by arginine codon with a site-directed mutagenesis (Papworth, C. et al., *Stratagies,* 9, 3, 1996) to construct an expression vector containing IFNα-2b gene. Vector pT14SSIα-2a was subjected to hybridization with the synthetic oligonucleotides of SEQ ID NOS: 19 and 20 containing the replaced codon to form a hybrid molecule and DNA amplification was performed using pfu (Stratagene, USA) and four nucleotide triphosphates (ATP, GTP, TTT, CTP) which extend said oligonucleotides in the 5'-3' direction.

Interferon α-2b sequence

| 17 | 18 | 19 | 20 | 21 | 22 | 23 | 24 | 25 | 26 | 27 | 28 | 29 | |
|---|---|---|---|---|---|---|---|---|---|---|---|---|---|
| Leu | Leu | Ala | Gln | Met | Arg | **Arg** | Ile | Ser | Leu | Phe | Ser | Cys | (SEQ ID NO:18) |
| CTC | CTG | GCA | CAG | ATG | AGG | **AGA** | ATC | TCT | CTT | TTC | TCC | TGC | (SEQ ID NO:19) |
| GCA | GGA | AGG | AAG | AGA | GAT | **TCT** | CCT | CAT | CTG | TGC | CAG | GAG | (SEQ ID NO:20) |

The amplified DNA fragment was recovered and an restriction enzyme DpnI was added thereto to remove unconverted plasmids completely.

*E. coli* XL-1 blue (Novagen, USA) was transformed with the modified plasmid. The base sequence of the DNA recovered from transformed colonies was determined, and thus obtained was plasmid pT14SSIα-2b which contained a gene having arginine in place of the 23$^{rd}$ amino acid lycine of IFNα2a.

Subsequently, *E. coli* BL21(DE3) was transformed with the modified vector pT14SSIα-2b to obtain a transformant designated *E. coli* HM10701 by using the same method described in Comparative Example 1. By analyzing the N-terminal amino acid sequence of the protein produced by culturing the transformant, it has been confirmed that IFNα-2b having the native amino acid sequence was expressed therefrom.

EXAMPLE 1

Construction of a Vector Containing Enterotoxin Signal Peptide Mutant (1) Construction of a Vector Containing [Thr$^4$]STII In order to modify a specific amino acid residue of the enterotoxin signal sequence peptide, a vector containing a polynucleotide encoding enterotoxin mutant signal sequence was prepared by site-directed mutagenesis as follows.

First, vector pT14SSIα-2a obtained in Comparative Example 1 was subjected to PCR using oligonucleotides of SEQ ID NOS: 22 and 23 to obtain a modified plasmid, wherein the 4$^{th}$ amino acid of the enterotoxin signal sequence is replaced with threonine (Thr), by the site-directed mutagenesis procedure described in Comparative Example 2.

```
                              (SEQ ID NO:21)
       Met Lys Lys Thr Ile Ala Phe Leu

                              (SEQ ID NO:22)
5'-GGTGATTTT ATG AAA AAG ACA ATC GCA TTT CTT C-3'

                              (SEQ ID NO:23)
3'-CCACTAAAA TAC TTT TTC TGT TAG CGT AAA GAA G-5'
```

Then, *E. coli* XL-1 blue (Novagen, USA) was transformed with the modified plasmid. The base sequence of DNA recovered from the transformed colonies was determined, and thus obtained was a plasmid which contained a gene encoding the enterotoxin signal sequence peptide having Thr in the 4$^{th}$ amino acid position thereof. The plasmid thus obtained was cleaved with XbaI and MluI, and then inserted into the XbaI/MluI section of vector pT14SSIα-2a to obtain vector pT14SSIα-2a-4T.

Subsequently, *E. coli* BL21(DE3) (Stratagene, USA) was transformed with vector pT14SSIα-2a-4T to obtain an *E. coli* transformant designated *E. coli* HM 10602.

Vector pT14SSIα-2a-4T was constructed using pT14SSIα-2b, and then transformed into *E. coli* BL21(DE3) (Stratagene, USA) to obtain an *E. coli* transformant designated *E. coli* HM 10702 by the same method described above.

(2) Construction of a Vector Containing [Thr$^4$, Gln$^{22}$]STII

Vector pT14SSIα-2a-4T obtained in step (1) was subjected to PCR using the oligonucleotides of SEQ ID NOS: 25 and 26, which were designed to substitute Gln codon for the 22$^{nd}$ amino acid of the enterotoxin signal peptide having Thr in its 4$^{th}$ position, in accordance with the site-directed mutagenesis procedure of step (1) to obtain a modified plasmid.

```
                                  (SEQ ID NO:24)
     Asp Ala Gln Ala Cys Asp Leu Pro

                                  (SEQ ID NO:25)
5'-CA ATT GCC CAA GCG TGT GAT CTG CCT-3'

                                  (SEQ ID NO:26)
3'-GT TTA CGG GTT CGC ACA CTA GAC GGA-5'
```

Then, *E. coli* XL-1 blue (Novagen, USA) was transformed with the modified plasmid. The base sequence of DNA recovered from transformed colonies was determined, and thus obtained was plasmid pT14SSIα-2a-4T22Q which contained a gene having Thr and Gln in the 4$^{th}$ and 22$^{nd}$ amino acid positions of the enterotoxin signal sequence, respectively. Subsequently, *E. coli* BL21(DE3) (Stratagen, USA) was transformed with vector pT14SSIα-2a-4T22Q by the same method described in step (1) to obtain a transformant designated *E. coli* HM 10604.

To modify the Shine-Dalgarno sequence of the modified enterotoxin signal sequence into SEQ ID NO: 9, vectors pT14SSIα-2a-4T and pT14SSIα-2a-4T22Q were subjected to the site-directed mutagenesis procedure described in step (2) using the oligonucleotides of SEQ ID NOS: 27 and 28 to obtain the desired modified plasmid.

Figure 4:
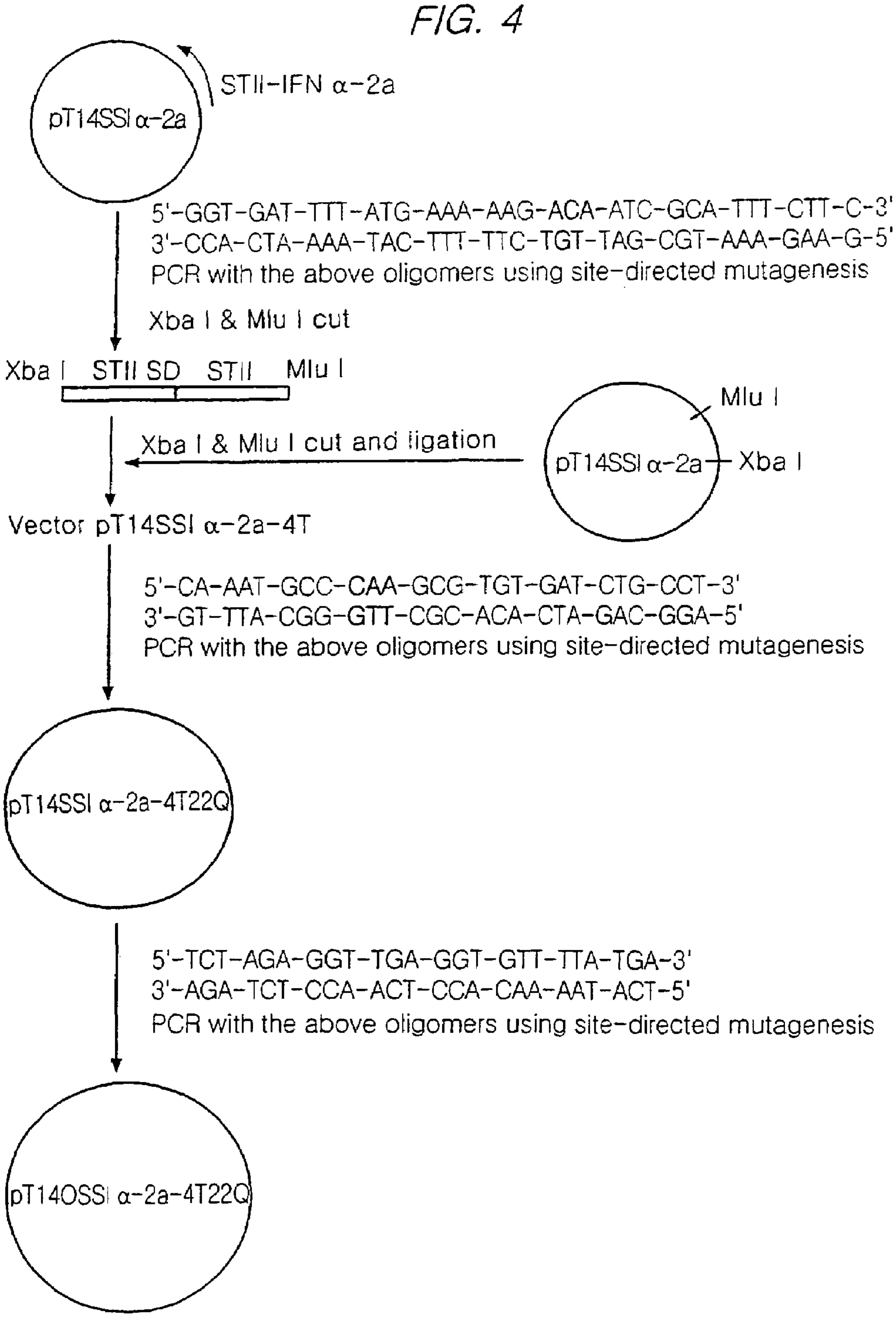
FIG. 4: the procedure for constructing vector pT140SSIα-2a-4T22Q.

*E. coli* XL-1 blue (Novagen, USA) was transformed with the modified plasmid. The base sequence of the DNA recovered from transformed colonies was determined, and thus obtained were plasmids pT14OSSIα-2a-4T and pT14OSSIα-2a-4T22Q having modified Shine-Dalgarno sequence of enterotoxin signal sequence. FIG. 4 represents the above procedure for constructing vector pT14OSSIα-2a-4T22Q.

*E. coli* BL21(DE3) was transformed with vector pT14OSSIα-2a-4T and pT14OSSIα-2a-4T22Q, respectively, to obtain a transformant designated *E. coli* HM 10603 and HM 10611, which were deposited in Korean Culture Collection of Microorganisms (KCCM) on Dec. 23, 1999 under accession numbers KCCM-10175 and KCCM-10176, respectively.

In addition, vectors pT14OSSIα-2b-4T and pT14OSSIα-2b-4T22Q were prepared by the same procedure as above using vector pT14SSIα-2b, which were used to transform *E. coli* BL21(DE3) to obtain transformants designated *E. coli* HM 10703 and HM 10711, respectively. *E. coli* transformants HM 10703 and HM 10711 were deposited in KCCM on Dec. 23, 1999 under accession numbers KCCM-10177 and KCCM-10178, respectively.

(3) Construction of a Vector Containing [Thr$^4$, Val$^{20}$, Gln$^{22}$] STII

To further substitute Val codon for the 20$^{th}$ amino acid of the enterotoxin signal sequence peptide having Thr and Gln in its 4$^{th}$ and 22$^{nd}$ amino acid positions, vectors pT14OSSIα-2a-4T22Q and pT14OSSIα-2b-4T22Q prepared in step (2) were subjected to PCR using the oligonucleotides of SEQ ID NOS: 29 and 30 by the site-directed mutagenesis procedure described in step (2), to obtain the desired modified plasmids designated pT14OSSIα-2a-4T20V22Q and pT14OSSIα-2b-4T20V22Q.

*E. coli* XL-1 blue was transformed with the modified plasmids. The base sequences of the DNAs recovered from transformed colonies were determined, and thus obtained were plasmids pT14OSSIα-2a-4T20V22Q and pT14OSSIα-2b-4T20V22Q which contained a gene having Thr, Val and Gln codons in places of the 4$^{th}$ Asp, 20$^{th}$ Asp and 22$^{nd}$ Tyr codons, respectively. *E. coli* BL21(DE3) was transformed with the plasmids to obtain thransformants designated *E. coli* HM 10612 and HM 10712, respectively.

EXAMPLE 2

Preparation of Thermostable Enterotoxin II Shine-Dalgarno Sequence Mutant

In order to reduce the number of bases between the ribosome binding site and initiation codon ATG of the modified *E. coli* thermostable enterotoxin II signal sequence within thermostable enterotoxin II Shine-Dalgarno sequence of the above-prepared expression vector, a modified plasmid was constructed by the site-directed mutagenesis procedure of Comparative Example 2.

Namely, to reduce the number of bases between the ribosome binding site GAGG and initiation codon ATG from 7 to 5, vector pT14OSSIα-2a-4T22Q prepared in Example 1 (2) was subjected to the site-directed mutagenesis procedure of Comparative Example 2 using the oligonucleotides of SEQ ID NOS: 31 and 32 to obtain a modified plasmid designated pT14NSSIα-2a-4T22Q. In addition, to reduce the number of bases between the ribosome binding site GAGG and initiation codon ATG to 4, vector pT14NSSIα-2a-4T22Q was subjected to by the site-directed mutagenesis procedure of Comparative Example 2 using the oligonucleotides of SEQ ID NOS: 33 and 34 to obtain a modified plasmid designated pT14MSSIα-2a-4T22Q.

*E. coli* XL-1 blue was transformed with the modified plasmids. The base sequences of the DNAs recovered from transformed colonies were determined, and thus obtained were IFNα expression plasmids pT14NSSIα-2a-4T22Q and pT14MSSIα-2a-4T22Q which respectively contained 5 and 4 bases between the ribosome binding site GAGG and initiation codon ATG. *E. coli* BL21(DE3) was transformed with the expression plasmids to obtain transformants designated HM 10613 and HM 10614, respectively.

EXAMPLE 3

Comparison of Expression Amount of IFNα-2

Transformants prepared in the above Comparative Examples and Examples were cultured in LB medium and then incubated in the presence of IPTG for 3 hours. Each of the cultures was centrifuged at 6,000 rpm for 20 min. to precipitate bacterial cells and the precipitate was treated by Osmotic shock method (Nossal, G. N., *J. Biol. Chem.,* 241:3055, 1966) as following.

The precipitate was suspended in a 1/10 volume of isotonic solution (20% sucrose, 10 mM Tris-Cl buffer containing 1 mM EDTA, pH 7.0). The suspension was allowed to stand at room temperature for 30 min, and then centrifuged to collect bacterial cells. The cells were resuspended in D.W. at 4° C. to extract the proteins present in the periplasm of the cells, and centrifuged to obtain a supernatant as a periplasmic solution. The IFNα-2 level in the periplasmic solution was assayed in accordance with ELISA method (Kato, K. et al., *J. Immunol.,* 116, 1554, 1976) using an antibody against the IFNα-2 (R&D, USA), which was calculated as the amount of the IFNα-2a produced per 1 l of culture. The results are shown in Table 1.

TABLE I

Comparision of expression amount of IFNα-2

| Transformant | Example | Expression Vector | Modified amino acid residue in STII | IFNα-2 Level in periplasm* |
|---|---|---|---|---|
| HM 10600 | Comp. Exam. 1 | PT14SIα-2a | | 82 ± 40 |
| HM 10601 | Comp. Exam. 1 | PT14SSIα-2a | | 325 ± 75 |
| HM 10701 | Comp. Exam. 2 | PT14SSIα-2b | | 288 ± 90 |
| HM 10602 | Example 1 (1) | pT14SSIα-2a-4T | $Thr^4$ | 550 ± 120 |
| HM 10603 | Example 1 (2) | pT14OSSIα-2a-4T | $Thr^4$ | 1,020 ± 135 |
| HM 10604 | Example 1 (2) | PT14SSIα-2a-4T22Q | $Thr^4$, $Gln^{22}$ | 680 ± 105 |
| HM 10611 | Example 1 (2) | pT14OSSIα-2a-4T22Q | $Thr^4$, $Gln^{22}$ | 1,220 ± 120 |
| HM 10612 | Example 1 (3) | pT14OSSIα-2a-4T20V22Q | $Thr^4$, $Val^{20}$, $Gln^{22}$ | 1,130 ± 180 |
| HM 10613 | Example 2 | pT14NSSIα-2a-4T22Q | $Thr^4$, $Gln^{22}$ | 750 ± 144 |
| HM 10614 | Example 2 | pT14MSSIα-2a-4T22Q | $Thr^4$, $Gln^{22}$ | 420 ± 100 |
| HM 10702 | Example 1 (1) | pT14SSIα-2b-4T | $Thr^4$ | 370 ± 90 |
| HM 10703 | Example 1 (2) | pT14OSSIα-2b-4T | $Thr^4$ | 735 ± 117 |
| HM 10711 | Example 1 (2) | pT14OSSIα-2b-4T22Q | $Thr^4$, $Gln^{22}$ | 1,070 ± 150 |
| HM 10712 | Example 1 (3) | pT14OSSIα-2b-4T20V22Q | $Thr^4$, $Val^{20}$, $Gln^{22}$ | 820 ± 160 |

*IFNα mg/100 $O.D_{600\ nm}$/L culture solution

EXAMPLE 4

Post-treatment and Purification

According to the procedure of Example 3, transformant *E. coli* HM 10611 prepared in Example 1(2) was cultured in LB medium and the culture was centrifuged for 6,000 rpm for 20 min. to harvest cells. The periplasmic solution was prepared from the cells by the Osmotic Shock method.

The periplasmic solution was adjusted to pH 5.0 to 5.5, adsorbed on an S-Sepharose (Pharmacia Inc., Sweden) column pre-equilibrated to pH 5.3, and then, the column was washed with 25 mM NaCl. IFNα-2 was eluted by sequentially adding acetic acid buffer solutions containing 50 mM, 100 mM, 200 mM and 1 M NaCl, respectively, and fractions containing IFNα-2 were collected and combined.

The combined fractions were subjected to Blue Sepharose (Pharmacia Inc., Sweden) column chromatography and eluted by adding to the column buffer solutions containing more than 2 M NaCl to obtain an active fraction.

The active fraction was dialyzed with a buffer, and finally subjected to resin column fractionation using a DEAE anion exchange resin column at pH 5.8 to obtain IFNα-2a having a purity of more than 99%. In addition, IFNα-2b was purified from transformant *E. coli* HM 10711 by repeating the above procedure.

Each of the purified IFNα-2a and IFNα-2b fractions was subjected to sodium dodecylsulfate polyacrylamide gel electrophoresis (SDS-PAGE) to determine the purity and approximate IFNα concentration, and then subjected to a conventional ELISA method as in Example 3 to determine the exact IFNα concentration in the periplasmic solution. In addition, it was confirmed by N-terminal amino acid sequence analysis that IFNα-2a and IFNα-2b were of the native types having no additional methionine.

EXAMPLE 5

Determination of IFNα-2a Molecular Weight Produced from Recombinant Cell Lines The expression and molecular weights of IFNα-2a and IFNα-2b produced from recombinant cell lines were determined by using SDS-PAGE and Western blotting.

Figure 5A:
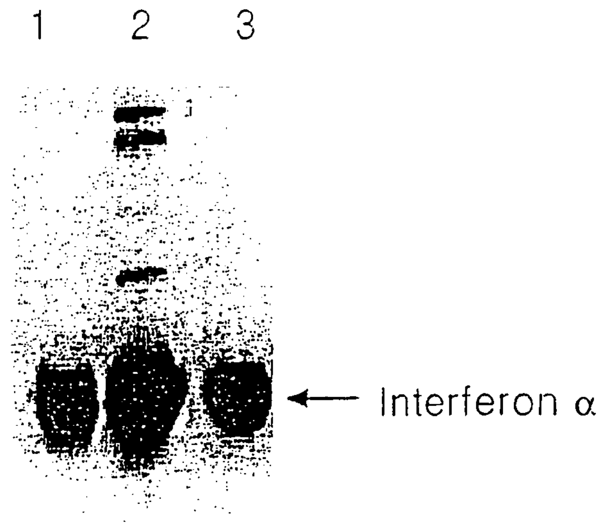
FIGS. 5*a* and 5*b*: the results of SDS-PAGE which verify the expression of IFNα-2a and the purity of the expressed IFNα-2a from recombinant cell lines, and the result of western blot analysis which verifies the molecular weight of expressed IFNα-2b, respectively.

First, the periplasmic fraction of transformant *E. coli* HM 10611 prepared in Example 4 and purified IFNα-2a obtained therefrom were subjected to SDS-PAGE using a commercial IFNα-2a product ($3\times10^6$ IU/ml) as a control according to the conventional method. FIG. 5*a* reproduces the SDS-PAGE result, wherein lane 1 shows the IFNα-2a control; lane 2, the periplasmic fraction of *E. coli* transformant HM 10611; and lane 3, the purified IFNα-2a. As can be seen from FIG. 5*a*, the purified IFNα-2a had the same molecular weight as that of the native IFNα-2a, and was present in the periplasmic fraction of transformant *E. coli* HM 10611 at a high level.

In addition, the periplasmic fraction of transformant *E. coli* HM 10711, a purified fraction obtained by subjecting the periplasmic solution to S-Sepharose column chromatography and the finally purified IFNα-2b were subjected to SDS-PAGE according to the conventional method.

Figure 5B:
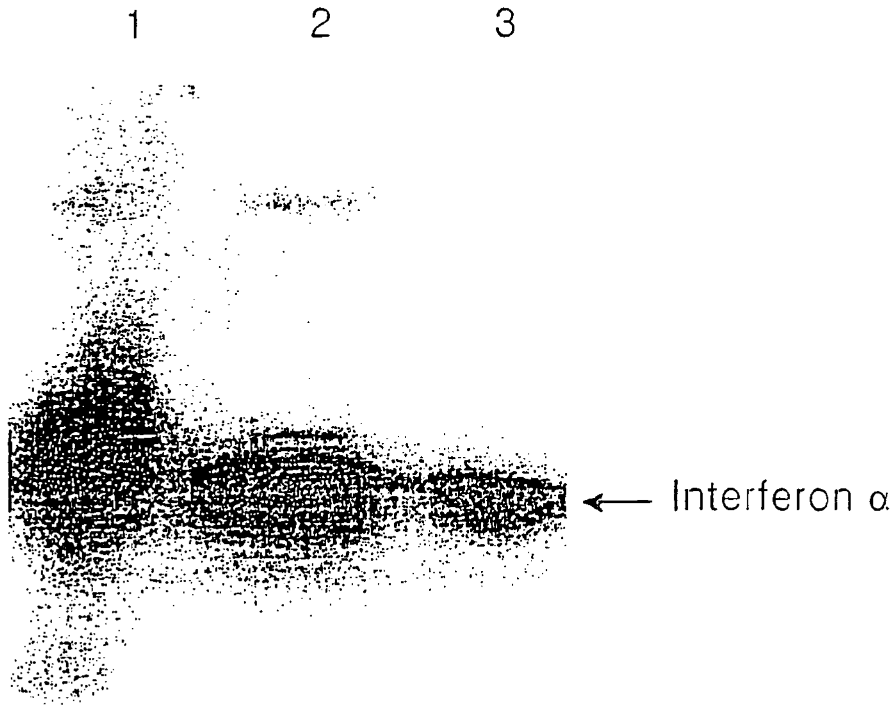

A nitrocellulose filter (Bio-Rad Lab, USA) was wetted with a buffer solution for blotting (170 mM glycine, 25 mM Tris•HCl [pH 8], 20% methanol) and the proteins separated on the gel were transferred onto the nitrocellulose filter over a period of 3 hours by using a blotting kit. The filter was kept in 1% Casein for 1 hour and washed three times with PBS containing 0.05% Tween 20. The filter was put in a rabbit anti-IFNα antibody (Chemicon, #AB1434, USA) solution diluted with PBS and reacted at room temperature for 2 hours. After reaction, the filter was washed 3 times with a PBST solution to remove unreacted antibody. Horseradish peroxidase-conjugated goat anti-rabbit IgG (Bio-Rad Lab., USA) diluted with PBS was added thereto and reacted at room temperature for 2 hour. The filter was washed with PBST, and a peroxidase substrate kit (Bio-Rad Lab., USA) solution was added thereto to develop a color reaction. The results from the above western blotting are shown in FIG. 5*b*, wherein lane 1 represents the periplasmic fraction of transformant *E. coli* HM 10711; lane 2, the fraction purified with S-Sepharose column chromatography; and lane 3, the final purified IFNα-2b.

As a result of Example, it is confirmed that a large quantity of soluble IFNα is expressed from the recombinant *E. coli* strains of the present invention.

What is claimed is:

1. An expression vector for the secretive production of human interferon alpha (hIFNα) comprising a polynucleotide encoding a modified thermostable enterotoxin II signal sequence and a polynucleotide encoding hIFNα ligated to the 3'-end thereof, wherein the modified thermostable enterotoxin II signal sequence is selected from the group consisting of:

a polypeptide obtained by replacing the $4^{th}$ asparagine of the amino acid sequence of SEQ ID NO: 3 with threonine;

a polypeptide obtained by replacing the $4^{th}$ asparagine and $22^{nd}$ tyrosine of the amino acid sequence of SEQ ID NO: 3 with threonine and glutamine, respectively;

a polypeptide obtained by replacing the $4^{th}$ and $20^{th}$ asparagines of the amino acid sequence of SEQ ID NO: 3 with threonine and valine, respectively, and;

a polypeptide obtained by replacing the $4^{th}$ asparagine, the $20^{th}$ asparagine and the $22^{nd}$ tyrosine of the amino acid sequence of SEQ ID NO: 3 with threonine, valine and glutamine, respectively.

2. The expression vector according to claim 1, wherein the polynucleotide encoding hIFNα codes for IFNα-2a of SEQ ID NO: 1 or IFNα-2b of SEQ ID NO:2.

3. The expression vector according to claim 1, which further comprises *E. coli* thermostable enterotoxin II Shine-Dalgarno sequence (SD sequence, SEQ ID NO:8) or a mutant thereof ligated to the front of the 5'-end of the polynucleotide encoding the modified thermostable enterotoxin II signal sequence, wherein the mutant has the nucleotide sequence of SEQ ID NO: 9.

4. The expression vector according to claim 1, which is selected from the group consisting of plasmids pT14SSIα-2a-4T, pT14OSSIα-2a-4T, pT14SSIα-2a-4T22Q, pT14OSSIα-2a-4T22Q, pT14OSSIα-2a-4T20V22Q, pT14NSSIα-2a-4T22Q, pT14MSSIα-2a-4T22Q, pT14SSIα-2b-4T, pT14OSSIα-2b-4T, pT14OSSIα-2b-4T22Q and pT14OSSIα-2b-4T20V22Q.

5. An *E. coli* transformed with the expression vector of any one of claims 1, 2, 3 and 4.

6. The *E. coli* according to claim 5, which is selected from the group consisting of *E. coli* BL21(DE3)/pT14SSIα-2a-4T (HM 10602), *E. coli* BL21(DE3)/pT14OSSIα-2a-4T (HM 10603; Accession NO: KCCM-10175), *E. coli* BL21(DE3)/pT14SSIα-2a-4T22Q (HM 10604), *E. coli* BL21(DE3)/pT14OSSIα-2a-4T22Q (HM 10611; Accession NO: KCCM-10176), *E. coli* BL21(DE3)/pT14OSSIα-2a-4T20V22Q (HM 10612), *E. coli* BL21(DE3)/pT14NSSIα-2a-4T22Q (HM 10613), *E. coli* BL21(DE3)/pT14MSSIα-2a-4T22Q (HM 10614), *E. coli* BL21(DE3)/pT14SSIα-2b-4T (HM 10702), *E. coli* BL21(DE3)/pT14OSSIα-2b-4T (HM 10703; Accession NO: KCCM-10177), *E. coli* BL21 (DE3)/pT14OSSIα-2b-4T22Q (HM 10711; Accession NO: KCCM-10178) and *E. coli* BL21(DE3)/pT14OSSIα-2b-4T20V22Q (HM 10712).

7. A process for secretively producing hIFNα having no additional methionine residue attached at the N-terminal comprising the steps of transforming an *E. coli* with an expression vector for the secretive production of hIFNα comprising a polynucleotide encoding a modified thermostable enterotoxin II signal sequence and a polynucleotide encoding hIFNα ligated to the 3'-end thereof; and culturing the transformed *E. coli*, wherein the modified thermostable enterotoxin II signal sequence is selected from the group consisting of:

a polypeptide obtained by replacing the $4^{th}$ asparagine of the amino acid sequence of SEQ ID NO: 3 with threonine;

a polypeptide obtained by replacing the $4^{th}$ asparagine and $22^{nd}$ tyrosine of the amino acid sequence of SEQ ID NO: 3 with threonine and glutamine, respectively;

a polypeptide obtained by replacing the $4^{th}$ and $20^{th}$ asparagines of the amino acid sequence of SEQ ID NO: 3 with threonine and valine: and a polypeptide obtained by replacing the $4^{th}$ asparagine, the $20^{th}$ asparagine and the $22^{nd}$ tyrosine of the amino acid sequence of SEQ ID NO: 3 with threonine, valine and glutamine, respectively.

8. The process according to claim 7, wherein the polynucleotide encoding hIFNα codes for IFNα-2a of SEQ ID NO: 1 or IFNα-2b of SEQ ID NO: 2.

9. The process according to claim 7, which said vector further comprises *E. coli* thermostable enterotoxin II SD sequence (SEQ ID NO:8) or a mutant thereof ligated to the front of the 5'-end of the polynucleotide encoding the modified thermostable enterotoxin II signal sequence, wherein the mutant has the nucleotide sequence of SEQ ID NO: 9.

10. The process according to claim 7, wherein the expression vector is selected from the group consisting of plasmids pT14SSIα-2a-4T, pT14OSSIα-2a-4T, pT14SSIα-2a-4T22Q, pT14OSSIα-2a-4T22Q, pT14OSSIα-2a-4T20V22Q, pT14NSSIα-2a-4T22Q, pT14MSSIα-2a-4T22Q, pT14SSIα-2b-4T, pT14OSSIα-2b-4T, pT14OSSIα-2b-4T22Q and pT14OSSIα-2b-4T20V22Q.

11. The process according to claim 7, wherein the transformed *e. coli* is selected from the group consisting of *E. coli* BL21(DE3)/pT14SSIα-2a-4T (HM 10602), *E. coli* BL21 (DE3)/pT14OSSIα-2a-4T (HM 10603; Accession NO: KCCM-10175), *E. coli* BL21(DE3)/pT14SSIα-2a-4T22Q (HM 10604), *E. coli* BL21(DE3)/pT14OSSIα-2a-4T22Q (HM 10611; Accession NO: KCCM-10176), *E. coli* BL21 (DE3)/pT14OSSIα-2a-4T20V22Q (HM 10612), *E. coli* BL21(DE3)/pT14NSSIα-2a-4T22Q (HM 10613), *E. coli* BL21(DE3)/pT14MSSIα-2a-4T22Q (HM 10614), *E. coli* BL21(DE3)/pT14SSIα-2b-4T (HM 10702), *E. coli* BL21 (DE3)/pT14OSSIα-2b-4T (HM 10703; Accession NO: KCCM-10177), *E. coli* BL21(DE3)/pT14OSSIα-2b-4T22Q (HM 10711; Accession NO: KCCM-10178) and *E. coli* BL21(DE3)/pT14OSSIα-2b-4T20V22Q (HM 10712).

* * * * *

```
                         SEQUENCE LISTING

<160> NUMBER OF SEQ ID NOS: 34

<210> SEQ ID NO 1
<211> LENGTH: 165
<212> TYPE: PRT
<213> ORGANISM: Homo sapiens

<400> SEQUENCE: 1

Cys Asp Leu Pro Glu Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125
```

-continued

```
Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 2
<211> LENGTH: 165
<212> TYPE: PRT
<213> ORGANISM: Homo sapiens

<400> SEQUENCE: 2

Cys Asp Leu Pro Glu Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 3
<211> LENGTH: 23
<212> TYPE: PRT
<213> ORGANISM: Escherichia coli

<400> SEQUENCE: 3

Met Lys Lys Asn Ile Ala Phe Leu Leu Ala Ser Met Phe Val Phe Ser
1               5                   10                  15

Ile Ala Thr Asn Ala Tyr Ala
            20


<210> SEQ ID NO 4
<211> LENGTH: 69
<212> TYPE: DNA
<213> ORGANISM: Artificial Sequence
<220> FEATURE:
<223> OTHER INFORMATION: DNA encoding a modified E. coli thermostable
      enterotoxin II ([Thr4] ST II)

<400> SEQUENCE: 4

atgaaaaaga caatcgcatt tcttcttgca tctatgttcg ttttttctat tgctacaaat     60

gcctacgcg                                                              69
```

-continued

```
<210> SEQ ID NO 5
<211> LENGTH: 69
<212> TYPE: DNA
<213> ORGANISM: Artificial Sequence
<220> FEATURE:
<223> OTHER INFORMATION: DNA encoding a modified E. coli thermostable
      enterotoxin II ([Thr4, Gln22] ST II)

<400> SEQUENCE: 5

atgaaaaaga caatcgcatt tcttcttgca tctatgttcg ttttttctat tgctacaaat     60

gcccaagcg                                                              69


<210> SEQ ID NO 6
<211> LENGTH: 69
<212> TYPE: DNA
<213> ORGANISM: Artificial Sequence
<220> FEATURE:
<223> OTHER INFORMATION: DNA encoding a modified E. coli thermostable
      enterotoxin II ([Thr4, Val20, Gln22] ST II)

<400> SEQUENCE: 6

atgaaaaaga caatcgcatt tcttcttgca tctatgttcg ttttttctat tgctacagtt     60

gcccaagcg                                                              69


<210> SEQ ID NO 7
<211> LENGTH: 69
<212> TYPE: DNA
<213> ORGANISM: Artificial Sequence
<220> FEATURE:
<223> OTHER INFORMATION: DNA encoding a modified E. coli thermostable
      enterotoxin II ([Thr4, Val20] ST II)

<400> SEQUENCE: 7

atgaaaaaga caatcgcatt tcttcttgca tctatgttcg ttttttctat tgctacagtt     60

gcctacgcg                                                              69


<210> SEQ ID NO 8
<211> LENGTH: 11
<212> TYPE: DNA
<213> ORGANISM: Escherichia coli

<400> SEQUENCE: 8

gaggtgattt t                                                           11


<210> SEQ ID NO 9
<211> LENGTH: 10
<212> TYPE: DNA
<213> ORGANISM: Artificial Sequence
<220> FEATURE:
<223> OTHER INFORMATION: Modified Shine-Dalgarno sequence of E. coli
      thermostable enterotoxin II

<400> SEQUENCE: 9

gaggtgtttt                                                             10


<210> SEQ ID NO 10
<211> LENGTH: 35
<212> TYPE: DNA
<213> ORGANISM: Artificial Sequence
<220> FEATURE:
<223> OTHER INFORMATION: primer for preparing the N-terminal of
      interferon alpha-2a

<400> SEQUENCE: 10
```

-continued cgccgccata tgtgtgatct gcctcaaacc cacag                35

<210> SEQ ID NO 11
<211> LENGTH: 36
<212> TYPE: DNA
<213> ORGANISM: Artificial Sequence
<220> FEATURE:
<223> OTHER INFORMATION: primer for preparing the C-terminal of
      interferon alpha-2a

<400> SEQUENCE: 11
accgaattcg gatcctcatt ccttacttct taaact                36

<210> SEQ ID NO 12
<211> LENGTH: 72
<212> TYPE: DNA
<213> ORGANISM: Artificial Sequence
<220> FEATURE:
<223> OTHER INFORMATION: primer for the preparation of the secretion
      sequence of E. coli thermostable enterotoxin II

<400> SEQUENCE: 12
tcatgaaaaa gaatatcgca tttcttcttg catctatgtt cgttttttct attgctacaa    60
atgcctacgc gt                                                         72

<210> SEQ ID NO 13
<211> LENGTH: 72
<212> TYPE: DNA
<213> ORGANISM: Artificial Sequence
<220> FEATURE:
<223> OTHER INFORMATION: primer for the preparation of the secretion
      sequence of E. coli thermostable enterotoxin II

<400> SEQUENCE: 13
acgcgtaggc atttgtagca atagaaaaaa cgaacataga tgcaagaaga aatgcgatat    60
tctttttcat ga                                                         72

<210> SEQ ID NO 14
<211> LENGTH: 38
<212> TYPE: DNA
<213> ORGANISM: Artificial Sequence
<220> FEATURE:
<223> OTHER INFORMATION: primer for preparing the N-terminal of
      interferon alpha-2a

<400> SEQUENCE: 14
acaaatgcct acgcgtgtga tctgcctcaa acccacag              38

<210> SEQ ID NO 15
<211> LENGTH: 36
<212> TYPE: DNA
<213> ORGANISM: Artificial Sequence
<220> FEATURE:
<223> OTHER INFORMATION: primer for preparing the C-terminal of
      interferon alpha-2a

<400> SEQUENCE: 15
accgaattcg gatcctcatt ccttacttct taaact                36

<210> SEQ ID NO 16
<211> LENGTH: 65
<212> TYPE: DNA
<213> ORGANISM: Artificial Sequence
<220> FEATURE:
<223> OTHER INFORMATION: primer for introducing Shine-Dalgarno sequence
      of E. coli ST II -continued

<400> SEQUENCE: 16
cggtttccct ctagaggttg aggtgtttta tgaaaaagaa tatcgcattt cttcttgcat 60
ctatg 65

<210> SEQ ID NO 17
<211> LENGTH: 36
<212> TYPE: DNA
<213> ORGANISM: Artificial Sequence
<220> FEATURE:
<223> OTHER INFORMATION: primer for introducing Shine-Dalgarno sequence of E. coli ST II

<400> SEQUENCE: 17
accgaattcg gatcctcatt ccttacttct taaact 36

<210> SEQ ID NO 18
<211> LENGTH: 13
<212> TYPE: PRT
<213> ORGANISM: Escherichia coli

<400> SEQUENCE: 18

Leu Leu Ala Gln Met Arg Arg Ile Ser Leu Phe Ser Cys
1 5 10

<210> SEQ ID NO 19
<211> LENGTH: 39
<212> TYPE: DNA
<213> ORGANISM: Artificial Sequence
<220> FEATURE:
<223> OTHER INFORMATION: oligonucleotide for preparing interferon alpha-2b

<400> SEQUENCE: 19
ctcctggcac agatgaggag aatctctctt ttctcctgc 39

<210> SEQ ID NO 20
<211> LENGTH: 39
<212> TYPE: DNA
<213> ORGANISM: Artificial Sequence
<220> FEATURE:
<223> OTHER INFORMATION: anti-sense of SEQ ID NO: 19

<400> SEQUENCE: 20
gaggaccgtg tctactcctc ttagagagaa aagaggacg 39

<210> SEQ ID NO 21
<211> LENGTH: 8
<212> TYPE: PRT
<213> ORGANISM: Artificial Sequence
<220> FEATURE:
<223> OTHER INFORMATION: 1st to 8th amino acids of [Thr4] ST II

<400> SEQUENCE: 21

Met Lys Lys Thr Ile Ala Phe Leu
1 5

<210> SEQ ID NO 22
<211> LENGTH: 34
<212> TYPE: DNA
<213> ORGANISM: Artificial Sequence
<220> FEATURE:
<223> OTHER INFORMATION: oligonucleotide for preparing [Thr4] ST II

<400> SEQUENCE: 22

-continued

```
ggtgatttta tgaaaaagac aatcgcattt cttc                              34


<210> SEQ ID NO 23
<211> LENGTH: 34
<212> TYPE: DNA
<213> ORGANISM: Artificial Sequence
<220> FEATURE:
<223> OTHER INFORMATION: anti-sense of SEQ ID NO: 22

<400> SEQUENCE: 23

gaagaaatgc gattgtcttt ttcataaaat cacc                              34


<210> SEQ ID NO 24
<211> LENGTH: 11
<212> TYPE: PRT
<213> ORGANISM: Artificial Sequence
<220> FEATURE:
<223> OTHER INFORMATION: 20th to 27th amino acids of [Gln22] ST II

<400> SEQUENCE: 24

Asn Ala Gln Ala Cys Asp Leu Pro Gln Thr His
1               5                   10


<210> SEQ ID NO 25
<211> LENGTH: 37
<212> TYPE: DNA
<213> ORGANISM: Artificial Sequence
<220> FEATURE:
<223> OTHER INFORMATION: oligonucleotide for preparing [Gln22] ST II

<400> SEQUENCE: 25

caaatgccca agcgtgtgat ctgcctcaaa cccacag                           37


<210> SEQ ID NO 26
<211> LENGTH: 37
<212> TYPE: DNA
<213> ORGANISM: Artificial Sequence
<220> FEATURE:
<223> OTHER INFORMATION: anti-sense of SEQ ID NO: 25

<400> SEQUENCE: 26

ctgtgggttt gaggcagatc acacgcttgg gcatttg                           37


<210> SEQ ID NO 27
<211> LENGTH: 24
<212> TYPE: DNA
<213> ORGANISM: Artificial Sequence
<220> FEATURE:
<223> OTHER INFORMATION: primer for preparing the modified
      Shine-Dalgarno sequence of SEQ ID NO: 9

<400> SEQUENCE: 27

tctagaggtt gaggtgtttt atga                                         24


<210> SEQ ID NO 28
<211> LENGTH: 24
<212> TYPE: DNA
<213> ORGANISM: Artificial Sequence
<220> FEATURE:
<223> OTHER INFORMATION: anti-sense of SEQ ID NO: 27

<400> SEQUENCE: 28

tcataaaaca cctcaacctc taga                                         24


<210> SEQ ID NO 29
<211> LENGTH: 42
```

-continued

```
<212> TYPE: DNA
<213> ORGANISM: Artificial Sequence
<220> FEATURE:
<223> OTHER INFORMATION: oligonucleotide for preparing [Val20] ST II

<400> SEQUENCE: 29

gtttttcta ttgctacagt tgcccaagcg tgtgatctgc ct                          42


<210> SEQ ID NO 30
<211> LENGTH: 42
<212> TYPE: DNA
<213> ORGANISM: Artificial Sequence
<220> FEATURE:
<223> OTHER INFORMATION: anti-sense of SEQ ID NO: 29

<400> SEQUENCE: 30

aggcagatca cacgcttggg caactgtagc aatagaaaaa ac                         42


<210> SEQ ID NO 31
<211> LENGTH: 25
<212> TYPE: DNA
<213> ORGANISM: Artificial Sequence
<220> FEATURE:
<223> OTHER INFORMATION: primer for preparing a modified Shine-Dalgarno
      sequence

<400> SEQUENCE: 31

tctagaggtt gaggttttta tgaaa                                            25


<210> SEQ ID NO 32
<211> LENGTH: 25
<212> TYPE: DNA
<213> ORGANISM: Artificial Sequence
<220> FEATURE:
<223> OTHER INFORMATION: anti-sense of SEQ ID NO: 31

<400> SEQUENCE: 32

tttcataaaa acctcaacct ctaga                                            25


<210> SEQ ID NO 33
<211> LENGTH: 24
<212> TYPE: DNA
<213> ORGANISM: Artificial Sequence
<220> FEATURE:
<223> OTHER INFORMATION: primer for preparing a modified Shine-Dalgarno
      sequence

<400> SEQUENCE: 33

tctagaggtt gaggttttat gaaa                                             24


<210> SEQ ID NO 34
<211> LENGTH: 23
<212> TYPE: DNA
<213> ORGANISM: Artificial Sequence
<220> FEATURE:
<223> OTHER INFORMATION: anti-sense of SEQ ID NO: 33

<400> SEQUENCE: 34

ttcataaaa cctcaacctc taga                                              23
```